(12) United States Patent
Labadie et al.

(10) Patent No.: US 8,380,288 B2
(45) Date of Patent: Feb. 19, 2013

(54) SYSTEM AND METHODS OF USING IMAGE-GUIDANCE FOR PROVIDING AN ACCESS TO A COCHLEAR OF A LIVING SUBJECT

(75) Inventors: Robert F. Labadie, Nasheville, TN (US); J. Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1694 days.

(21) Appl. No.: 11/413,254

(22) Filed: Apr. 28, 2006

(65) Prior Publication Data

US 2006/0247517 A1 Nov. 2, 2006

Related U.S. Application Data

(60) Provisional application No. 60/676,436, filed on Apr. 29, 2005.

(51) Int. Cl.
*A61B 5/05* (2006.01)
(52) U.S. Cl. ........ 600/426; 600/407; 600/414; 600/424; 600/425; 600/427
(58) Field of Classification Search .................. 600/414, 600/426
See application file for complete search history.

(56) References Cited

U.S. PATENT DOCUMENTS

| 5,371,778 | A | * | 12/1994 | Yanof et al. ........................ 378/4 |
| 5,394,875 | A | * | 3/1995 | Lewis et al. .................... 600/445 |
| 7,366,562 | B2 | * | 4/2008 | Dukesherer et al. .......... 600/424 |
| 7,646,899 | B2 | * | 1/2010 | Fitzpatrick .................... 382/128 |
| 7,899,512 | B2 | | 3/2011 | Labadie et al. |
| 2002/0019669 | A1 | | 2/2002 | Berrang et al. |
| 2005/0085715 | A1 | | 4/2005 | Dukesherer et al. |

FOREIGN PATENT DOCUMENTS

WO WO 2004/100767 A2 11/2004

OTHER PUBLICATIONS

Caversaccio M. et al., Valuable use of computer-aided surgery in congenital bony aural atresia. J Laryngol Otol 2003;117:241-8.
Edwards P.J, et al., Design and evaluation of a system for microscope-assisted guided interventions (MAGI). IEEE Trans Med Imag 2000;19:1082-1093.
Fenlon MR, Jusczyzck AS, Edwards PJ, and King AP. Locking acrylic resin dental stent for image guided surgery. J of Prosthet Dent 2000;83:482-5.
Fitzpatrick J.M. et al., Predicting error in rigid-body, point-based registration. IEEE Trans Med Imaging 17, 694-702, 1998.
Kronenberg J. et al., The suprameatal approach: an alternative surgical approach to cochlear implantation. Otol Neurotol 2004;25:41-45.
Raabe A. et al., Laser surface scanning for patient registration in intracranial image-guided surgery. Nuerosurgery 2002;50:797-803.

(Continued)

*Primary Examiner* — Tse Chen
*Assistant Examiner* — Vani Gupta
(74) *Attorney, Agent, or Firm* — Morris, Manning & Martin, LLP; Tim Tingkang Xia, Esq.

(57) ABSTRACT

A system and methods for providing an access to a cochlea of a living subject. In one embodiment of the present invention, a method comprises the steps of operating a surgical instrument towards a region of interest of the living subject for opening an access to the cochlea of the living subject from the lateral edge of the skull of the living subject to the cochlea of the living subject, and intra-operatively monitoring at least a part of the surgical instrument so that the surgical instrument is operated substantially along a predetermined path.

14 Claims, 7 Drawing Sheets

OTHER PUBLICATIONS

Raine C.H., et al., How we do it: Using a surgical navigation system in the management of the ossified cochlea. Cochlear Implants International 2003;4:96-101.

Sargent E.W. et al., Middle cranial fossa surgery with image-guided instrumentation. Otolaryngol Head Neck Surg 1997;117:131-4.

Roberts, David W., et al. "A frameless sterotaxic integration of computerized tomographic graphic imaging and the operating microscope" J Neurosurg 65:545-549, (1986).

Weinberg, Jeffrey S. et al. "Surgical management of brain metastases" Current Oncology Reports 2001, 3:476-483.

Wisoff, Jeffrey H. et al. "Current neurosurgical management and the impact of the extent of resection in the treatment of malignant gliomas of childhood: a report of the Children's Cancer Group trial No. CCG-945" J of Neurosurg 89:52-59 (1998).

Schlaier, M.D., J. et al. "Registration accuracy and practicability of laser-directed surface matching" Computer Aided Surgery 2002; 7:284-290.

Labadie, Robert F. et al. "In vitro assessment of image-guided otologic surgery: Submillimeter accuracy within the region of the temporal bone" Otolaryngol Head Neck Surg 2005; 132:435-442.

Labadie, R.F. et al. "Image-Guided Otologic Surgery" Elsevier Science, International Congress Series 1256 (2003) 627-632.

Labadie, Robert F. et al. "Submillimetric Target-Registration Error using a Novel, Non-Invasive Fiducial System for Image Guided Otologic Surgery" Computer Aided Surgery, Biomedical Paper 2004; 9(4): 145-153.

Wang, Matthew Y. et al. "An automatic technique for finding and localizing externally attached markers in CT and MR volume images of the head" IEEE Trans Biomed Eng vol. 43, No. 6, Jun. 1996, pp. 627-637.

Cohen, Noel L. et al. "Medical or surgical complications related to the nucleus multichannel cochlear implant" Ann Otol Rhinol Laryngol 1988;97:8-13.

Canadian Office Action dated Aug. 8, 2012.

* cited by examiner

SYSTEM AND METHODS OF USING IMAGE-GUIDANCE FOR PROVIDING AN ACCESS TO A COCHLEAR OF A LIVING SUBJECT

CROSS-REFERENCE TO RELATED PATENT APPLICATION

This application claims the benefit, pursuant to 35 U.S.C. §119(e), of U.S. provisional patent application Ser. No. 60/676,436, filed Apr. 29, 2005, entitled "System and Methods of Using Image-Guidance for Placement of Cochlear Stimulator Devices, Drug Carrier Devices, or the Like," by Robert F. Labadie, and J. Michael Fitzpatrick, which is incorporated herein by reference in its entirety.

This application is related to a copending U.S. patent application entitled "System And Method For Surgical Instrument Disablement Via Image-Guided Position Feedback", U.S. patent application Ser. No. 11/079,898, filed 14 Mar. 2005 with the same applicants and assignee as the present invention. The disclosure of the above identified copending applications is incorporated herein by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [10] represents the 10th reference cited in the reference list, namely, Labadie R F, Fenlon M, Devikalp H, et al. Image-guided otologic surgery. Computer Assisted Radiology and Congress and Exhibition (eds: Lemke H U, Vannier M W, Inamura K, Farman A G, Doi K, Reiber J H C) pp. 627-32. Elsevier Science, Amsterdam, The Netherlands, 2003.

STATEMENT OF FEDERALLY-SPONSORED RESEARCH

The present invention was made with Government support under a contract R21 EB02886-01 awarded by the National Institute of Biomedical Imaging and Bioengineering. The United States Government may have certain rights to this invention pursuant to this grant.

FIELD OF THE INVENTION

The present invention generally relates to image-guided surgery, and more particularly to a system and methods of using image-guidance for providing an access to a cochlea of a living subject for performing a medical procedure.

BACKGROUND OF THE INVENTION

Image-guided surgery (hereinafter "IGS") technology has been clinically available since the mid-1980's [1]. Analogous to a global positioning system (hereinafter "GPS"), IGS facilitates intra-operative surgical navigation by linking pre-operative radiographs to intra-operative anatomy. Central to the IGS process is registration—the linking of the radiographic images to the patient. To achieve high accuracy the registration is based on fiducial markers are identified in both the radiographs and on the patient. A mathematical transformation matrix is created to optimize the alignment of the fiducial markers. This same transformation matrix is then applied to all information in the radiograph allowing an overlay of the radiograph onto the patient's physical anatomy. This information is typically presented to the surgeon via a video monitor; a pointer placed within the surgical field is linked to a cursor on the monitor to show the corresponding radiographic position in axial, saggital, and coronal sections.

IGS is widely used in neurosurgery where the gold standard fiducial is a rigidly affixed N-frame. Screwed directly into the cranium, the N-frame is secured before imaging studies are obtained and remains in place throughout surgical intervention. Such stereotactic frames are invasive and cumbersome. However, given a life-threatening disease such as a malignant brain tumor, they are tolerated by patients. Neurosurgical studies have shown that IGS decreases operative time [2] and allows more complete resection of pathologic tissue while minimizing collateral damage [3].

As applied to otology and neurotology, IGS has found limited use. Isolated case reports describe their use in patients with unusual anatomy. Utilizing a modified neurosurgical unit, Sargent and Bucholz reported on IGS for middle cranial fossa approaches [4]. Raine et al. utilized an IGS system for split-electrode cochlear implant placement in a patient with cochlear ossification [5]. In perhaps the most widespread use, Caversaccio et al. reported their series of aural atresia repair using IGS guidance [6].

The reasons that IGS technology has found limited clinical application in otology/neurotology remain unclear. Hypothetically, its use has been stalled by the need for non-invasive, yet accurate, fiducial systems. To achieve submillimetric IGS accuracy—necessary to prevent damage to vital structures within the temporal bone—bone-affixed fiducial systems have been necessary. At present, less invasive fiducial systems are less accurate; skin-affixed markers achieve accuracies in the range of 1.5 mm and laser skin contouring achieves accuracies in the range of 2.5 mm [7, 8].

Therefore, a heretofore unaddressed need still exists in the art to address the aforementioned deficiencies and inadequacies.

SUMMARY OF THE INVENTION

In one aspect, the present invention relates to a method for providing an access to the cochlea of a living subject, where the access to the cochlea of the living subject is a single passage from the lateral edge of the skull to the cochlea. In one embodiment, the method includes the steps of non-invasively placing a plurality of fiducial markers surrounding the cochlea of the living subject, and pre-operatively acquiring an image volume from the cochlea of the living subject, where the pre-operatively acquired image volume contains the image of the plurality of fiducial markers. In one embodiment, the non-invasively placing step comprises the step of mounting a locking dental acrylic resin splint (LADS) with an attached fiducial frame onto a maxilla of the living subject, where the fiducial frame is adapted for receiving the plurality of fiducial markers. The pre-operatively acquiring step is performed with an imaging acquisition device.

The method further includes the steps of identifying a centroid of each fiducial marker from the pre-operatively acquired image volume, pre-operatively measuring a location of each fiducial marker in an anatomic space of the cochlea of the living subject, registering the identified centroid of each fiducial marker in the pre-operatively acquired image volume to the pre-operatively measured location of the corresponding fiducial marker in the anatomic space so as to determine a registration transformation.

Furthermore, the method includes the steps of operating a surgical instrument along a predetermined path to open an access to the cochlea of the living subject, the surgical instrument having a distal end portion, tracking the distal end portion of the surgical instrument through a first optical emitter attached to the optical instrument and an optical tracker adapted for receiving optical signal from the first optical emitter, and intra-operatively guiding the surgical instrument through visualizing a location of the distal end portion of the surgical instrument in the pre-operatively acquired image volume.

The pre-operatively measuring step is performed with a localizing probe, where the localizing probe is coupled with the first optical emitter.

The operating step, in one embodiment, is performed by a human being. In another embodiment, the operating step is performed at least in part by a man-made device such as a robot.

In one embodiment, the intra-operatively guiding step comprises the steps of intra-operatively monitoring the location of the distal end portion of the surgical instrument in the anatomic space of the cochlea of the living subject, and mapping the intra-operatively monitored location of the distal end portion of the surgical instrument in the anatomic space onto a corresponding location in the pre-operatively acquired image volume by an inverse of the registration transformation, where the intra-operatively monitoring step is performed with the first optical emitter and the optical tracker.

Moreover, the method includes the step of intra-operatively tracking at least a portion of the skull of the living subject through a second optical emitter attached to LADS and the optical tracker adapted for receiving optical signal from the second optical emitter.

Additionally, the method includes the step of disabling the surgical instrument when the surgical instrument departs from the predetermined path.

The method may also include the step of performing a therapeutic medical procedure or a diagnosis medical procedure through the access to the cochlea of the living subject. The therapeutic medical procedure comprises a medical procedure for placement of one of a cochlear implant, a drug delivery system, a carrier device, a medical detecting system, a medical treatment system, and any combination of them. The diagnosis medical procedure comprises a medical procedure for using a medical device to detect and collect information related to the living subject.

In another aspect, the present invention relates to a system for providing an access to the cochlea of a living subject. In one embodiment, the system has means for non-invasively placing a plurality of fiducial markers surrounding the cochlea of the living subject. In one embodiment, the placing means comprises a locking dental acrylic resin splint (LADS) mountable to a maxilla of the living subject, wherein the LADS includes a central portion with an extension at a predetermined position, and two lateral portions attached to the central portion, and a fiducial frame attachable to the LADS by the extension for receiving the plurality of fiducial markers.

The system also has an imaging acquisition device for pre-operatively acquiring an image volume from the cochlea of the living subject, the pre-operatively acquired image volume containing the image of the plurality of fiducial markers. In one embodiment, the imaging acquisition device comprises a CT scanning device.

The system further has a surgical instrument having a distal end portion for opening an access to the cochlea of the living subject. In one embodiment, the surgical instrument comprises a drill, and the distal end portion of the surgical instrument comprises the tip of the drill. In another embodiment, the surgical instrument comprises a surgical scalpel, and the distal end portion of the surgical instrument comprises the cutting portion of the surgical scalpel.

Furthermore, the system has an infrared tracking system for pre-operatively measuring a location of each fiducial marker and intra-operatively monitoring a location of the distal end portion of the surgical instrument in the anatomic space of the cochlea of the living subject. The infrared tracking system comprises a first optical emitter attachable to the surgical instrument, and a second optical emitter attachable to the LADS, and an optical tracker adapted for receiving optical signals from the first optical emitter and the second optical emitter, respectively. In one embodiment, each of the first and second optical emitters comprises an infrared emitter.

Moreover, the system has a controller for receiving and processing data related to the pre-operatively acquired image volume, the pre-operatively measured location of each fiducial marker and the intra-operatively monitored location of the distal end portion of the surgical instrument so as to guide the surgical instrument along a predetermined path to open an access to the cochlea of the living subject. The controller, in one embodiment, is programmed to perform the steps of identifying a centroid of each fiducial marker in the pre-operatively acquired image volume, registering the identified centroid of each fiducial marker in the pre-operatively acquired image volume to the pre-operatively measured location of the corresponding fiducial marker in the anatomic space so as to determine a registration transformation, and mapping the intra-operatively monitored location of the distal end portion of the surgical instrument in the anatomic space onto a corresponding location in the pre-operatively acquired image volume by an inverse of the registration transformation, thereby intra-operatively displaying the location of the distal end portion of the surgical instrument. Furthermore, the controller is programmed to perform the step of disabling the surgical instrument when the surgical instrument departs from the predetermined path.

Additionally, the system has an image display device in communication with the controller for displaying the location of the distal end portion of the surgical instrument. The image display device in one embodiment comprises a monitor.

In yet another aspect, the present invention relates to a method for providing an access to the cochlea of a living subject. The access to the cochlea of the living subject is a single passage from the lateral edge of the skull to the cochlea. The method in one embodiment comprises the steps of providing a platform and a surgical instrument guide, pre-operatively determining a location for positioning the platform proximate to the cochlea of a living subject, positioning the platform proximate to the cochlea of a living subject to the pre-operatively determined location, operating a surgical instrument towards a region of interest of the living subject, where the surgical instrument has a distal end portion in operation reaching the region of interest for opening an access to the cochlea of the living subject, intra-operatively guiding the surgical instrument through the surgical instrument guide, and intra-operatively monitoring at least a location of the distal end portion of the surgical instrument so that the surgical instrument is operated substantially along a predetermined path.

The method further comprises the step of performing a therapeutic medical procedure or a diagnosis medical procedure through the access to the cochlea of the living subject. The therapeutic medical procedure comprises a medical procedure for placement of one of a cochlear implant, a drug delivery system, a carrier device, a medical detecting system, a medical treatment system, and any combination of them. The diagnosis medical procedure comprises a medical procedure for using a medical device to detect and collect information related to the living subject.

The method also comprises the step of disabling the surgical instrument when the surgical instrument departs from the predetermined path.

In one embodiment, the platform comprises a fiducial frame with at least one fiducial marker, where the fiducial frame comprises a customized fiducial frame. The operating step is performed by a human being, or at least in part by a man-made device such as a robot. The surgical guide includes an infrared tracking system. The pre-operatively determining step is performed with a registration procedure. The intra-operatively monitoring step is performed with an image-guided procedure.

In a further aspect, the present invention relates to a system for providing an access to the cochlea of a living subject. The access to the cochlea of the living subject is a single passage from the lateral edge of the skull to the cochlea. In one embodiment, the system has a platform, means for pre-operatively determining a location for positioning the platform proximate to the cochlea of the living subject, means for positioning the platform proximate to the cochlea of the living subject to the pre-operatively determined location, a surgical instrument guide for guiding a surgical instrument towards a region of interest of the living subject, wherein the surgical instrument has a distal end portion in operation reaching the region of interest first, for opening an access to the cochlea of the living subject, and means for intra-operatively monitoring at least a location of the distal end portion of the surgical instrument so that the surgical instrument is operated substantially along a predetermined path.

The system further has means for performing a medical procedure through the access. In one embodiment, the means for performing a medical procedure comprises a cochlea implant, a drug delivery system, a carrier device, a medical detecting system, a medical treatment system, and any combination of them.

The platform comprises a fiducial frame with at least one fiducial marker, where the fiducial frame comprises a customized fiducial frame.

The surgical instrument guide comprises an infrared tracking system. In one embodiment, the surgical instrument comprises a drill, and the distal end portion of the surgical instrument comprises the tip of the drill. In another embodiment, the surgical instrument comprises a surgical scalpel, and the distal end portion of the surgical instrument comprises the cutting portion of the surgical scalpel.

The means for pre-operatively determining a location comprises a controller and/or software stored on a computer readable medium for causing the controller to perform at least a registration procedure.

The intra-operatively monitoring means comprises a controller and/or software stored on a computer readable medium for causing the controller to perform at least an image-guided procedure. The intra-operatively monitoring means further comprises an image displaying device in communication with the controller.

The system further has means for disabling the surgical instrument when the surgical instrument departs from the predetermined path.

In yet a further aspect, the present invention relates to a method for providing an access to the cochlea of a living subject. In one embodiment, the method includes the steps of operating a surgical instrument towards a region of interest of the living subject for opening an access to the cochlea of the living subject from the lateral edge of the skull of the living subject to the cochlea of the living subject, and intra-operatively monitoring at least a part of the surgical instrument so that the surgical instrument is operated substantially along a predetermined path.

The method further includes the step of disabling the surgical instrument when the surgical instrument departs from the predetermined path.

The method also includes the step of intra-operatively and independently monitoring a position of the skull of the living subject.

These and other aspects of the present invention will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Figure 1:
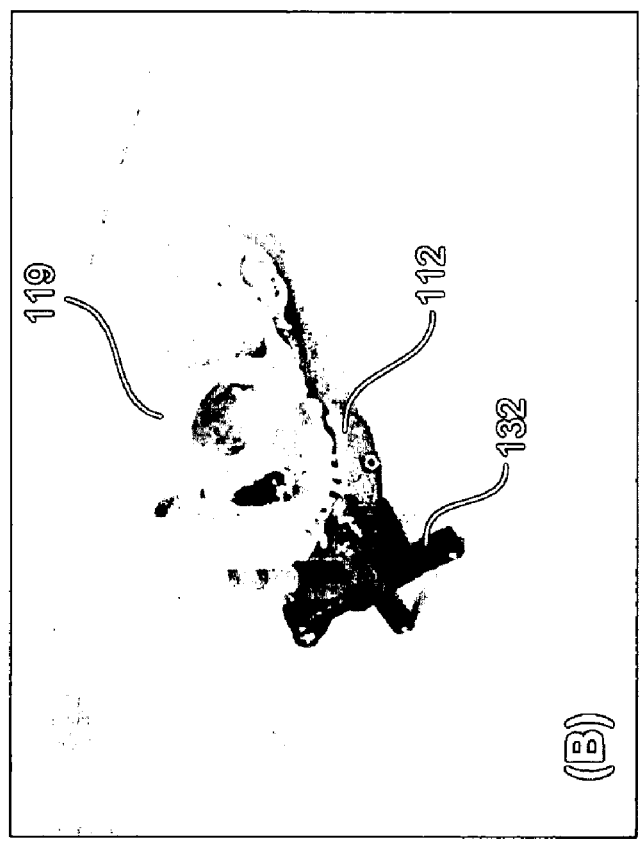
FIG. 1 shows (A) an EarMark™ fiducial frame system worn during pre-operative radiographic imaging, and (B) an infrared emitter worn during surgery. In panel (A), fiducial markers placed on the horizontal bar and vertical bar are arranged to surround the surgical field of interest—the temporal bone. The fiducial frame is affixed to the maxillary dentition via a customized mouthguard—a locking dental acrylic resin splint (hereinafter "LADS"). In panel (B), the infrared emitter is attached to the LADS as a rigid extension of the EarMark™ fiducial frame system, which allows unimpeded access to the temporal bone during surgery.
Figure 1:
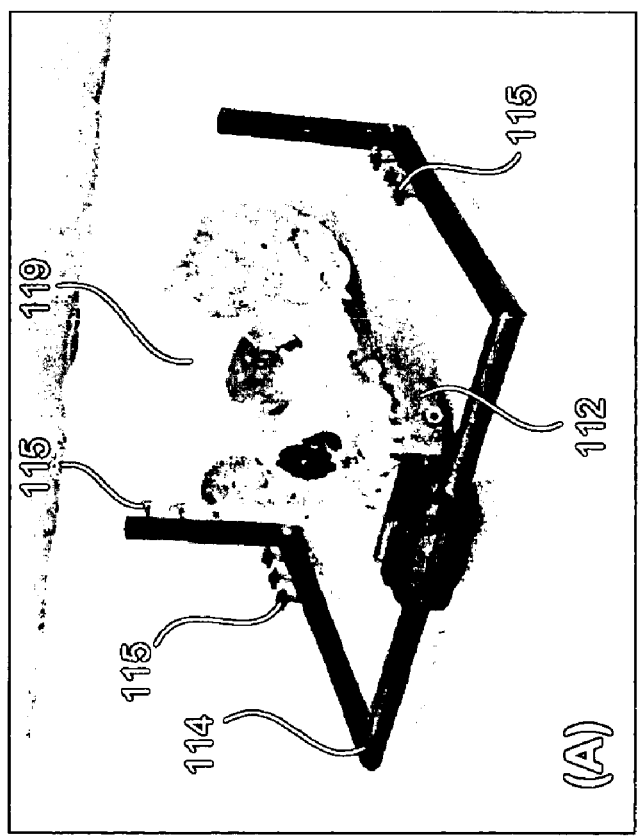

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which has no influence on the scope of the invention. Additionally, some terms used in this specification are more specifically defined below.

DEFINITIONS

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing rat, gerbil, monkey or the like.

The term "cochlea," as used herein, refers to a spiral-shaped cavity of an inner ear that resembles a snail-like shell and contains nerve endings essential for hearing. The snail-like structure is buried deeply within the temporal bone and located on either sides of the skull. A cochlea includes three fluid-filled chambers: scala tympani and scala vestibuli (both of which contain perilymph), and scala media (which contains endolymph).

The term "cochlear implant", as used herein, refers to a device that is placed into scala tympani of a cochlea to provide sound perception for deaf or hearing impaired individuals.

Overview of the Invention

The widespread use of IGS in otologic surgery has been limited by the need for a system that achieves the necessary level of accuracy with an easy-to-use, non-invasive fiducial marker system. The inventors according to the present invention have developed such a system and related methods/procedures, where submillimetric accuracy is achieved. With this system, image-guided otologic surgery permits accurate access to the middle ear via the facial recess using a single drill hole from the lateral aspect of the mastoid cortex so as to perform a medical procedure. The medical procedure includes a therapeutic medical procedure or a diagnosis medical procedure. The therapeutic medical procedure may be corresponding to a medical procedure for placement of one of a cochlear implant, a drug delivery system, a carrier device, a medical detecting system, a medical treatment system, and any combination of them. The diagnosis medical procedure may comprise a medical procedure for using a medical device to detect and collect information related to a patient.

In accordance with the purposes of this invention, as embodied and broadly described herein, this invention, in one aspect, relates to a method for providing an access to the cochlea of a living subject, comprising the steps of operating a surgical instrument towards a region of interest of the living subject for opening an access to the cochlea of the living subject from the lateral edge of the skull of the living subject to the cochlea of the living subject and intra-operatively monitoring at least a part of the surgical instrument so that the surgical instrument is operated substantially along a predetermined path. Accordingly, the image-guided otologic surgery performed based on the present invention provides an access, in the form of a single passage, to the middle ear via the facial recess in a minimally-invasive, percutaneous fashion.

Figure 2:
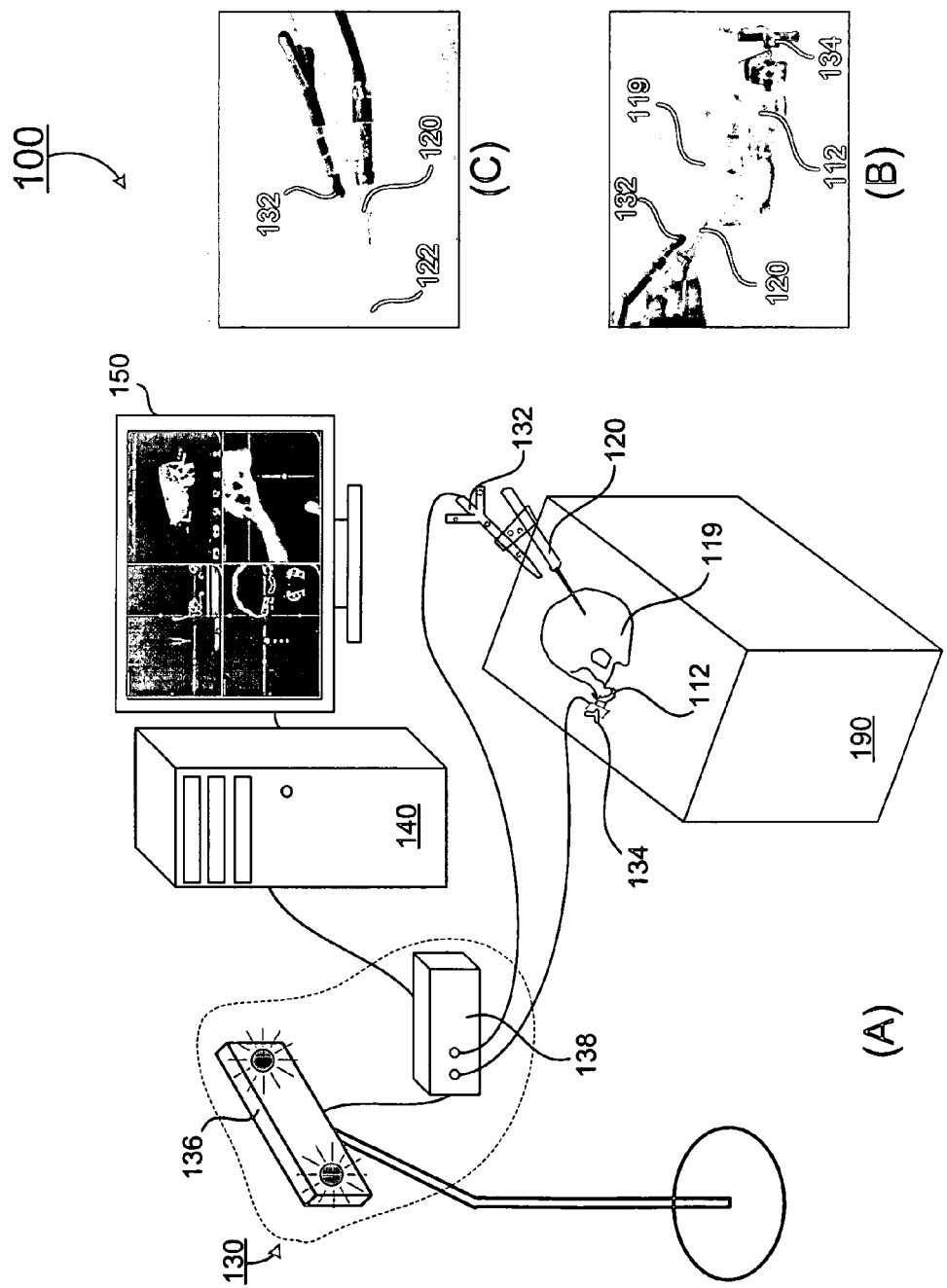
FIG. 2 shows schematically an image-guided otologic surgery system according to one embodiment of the present invention: (A) the system including an infrared tracking system, a surgical tool, a computer, and a video monitor, (B) a photograph of a skull with the surgical tool coupled with an infrared emitter, and (C) a photograph of the surgical tool coupled with the infrared emitter.

Another aspect of the present invention provides a system of an image-guided otologic surgery for providing an access to the cochlea of a living subject to perform a medical procedure. Referring to FIGS. 1 and 2, the system 100 includes means for non-invasively placing a plurality of fiducial markers surrounding the cochlea of the patient. As shown in FIG. 1A, the placing means 110 has an LADS 112 mounted to a maxilla of the living subject and a fiducial frame 114 attached to the LADS 112. The LADS 112 resembles an athletic mouthguard but comprises three pieces instead of one: a central piece with an extension at a predetermined position, which engages the biting surfaces of the teeth of the patient, as well as right and left buccal pieces, which engage the lateral surfaces of the teeth of the patient. The three pieces are attached together with screws which lock the components around the crowns of the teeth of the living subject thereby fixing the mouthpiece reliably in place while allowing it to be removed and replaced in the same position and orientation. The fiducial frame 114 is a lightweight yet rigid frame which extends to surround the external ears of the living subject for placing the plurality of fiducial markers 115 in close proximity to the temporal bone. As shown in FIG. 1A, the fiducial frame 114 is corresponding to an EarMark™ system developed by the inventors [9-11]. The EarMark™ system 114 is secured to the skull 119 of the living subject by mounting the LADS 112 onto the maxilla of the patient. Rigid fixation of the fiducial markers 115 to the EarMark™ system 114 is advantageous because it avoids drilling into the skull 119. In this embodiment, twelve fiducial markers 115, such as Acustar® of Z-Kat, Inc., Hollywood, Fla., are received in the EarMark™ system 114, and placed around the cochlea of the living subject in a non-invasive fashion. Using the EarMark™ system with a commercially-available IGS system, submillimetric accuracy within the temporal bone is demonstrated. In one embodiment, for over 234 target registrations, mean target registration error (TRE) was 0.76 mm with a standard deviation of 0.23 mm. The LADS and the fiducial frame may be customized for a specific patient.

Furthermore, the system 100 includes an image acquisition device (not shown), such as a CT (computed tomography) imaging scanner or a MR (magnetic resonance) imaging scanner, for pre-operatively acquiring an image volume, i.e., a three-dimensional (hereinafter "3D") radiographic image, which contains the fiducial markers from the ear portion of the patient. In one embodiment, the image volume, such a CT image, is acquired using clinically applicable, temporal-bone algorithms with scan thickness of about 0.5 mm.

Moreover, the system 100 includes a surgical instrument 120 having a distal end portion 122 for opening an access to the cochlea of the patient. The surgical instrument 120 can be a high-speed surgical drill or a surgical scalpel. For a surgical drill, the distal end portion is corresponding to the tip of the drill. For a surgical scalpel, the distal end portion is corresponding to the cutting portion of the surgical scalpel. Other types of surgical instruments can also be used to practice the present invention. The surgical instrument can be operated by a surgeon or at least partially by a man-made device such as a robot.

Additionally, the system 100 has an infrared tracking system for pre-operatively measuring a location of each fiducial marker and intra-operatively monitoring a location of the distal end portion of the surgical instrument in the anatomic space of the patient. In the embodiment, the infrared tracking system includes a first optical emitter 132 attached to the surgical instrument 120 as shown in FIGS. 2A-2C, a second optical emitter 134 attached to the LADS 112 as shown in FIGS. 1B, 2A and 2B, respectively. The infrared tracking system 130 also includes an optical tracker 130 having a position sensor 136, and a processor 138. Each of the first and second optical emitter 132 and 134 can be an infrared emitter adapted for emitting infrared light and is communicable to the processor 138 through coupling means such as cable. The optical tracker 130 is adapted for receiving optical signals emitted from the first and second optical emitter 132 and 134 so as to detect the position of each of the first and second optical emitter 132 and 134. In one embodiment, a commercially available infrared tracking system (Polaris®, Northern Digital Inc., Waterloo, Canada) is employed to measure the location of each fiducial marker and the location of the distal end portion of the surgical instrument in the anatomic space of the patient. Other tracking systems can also be used to practice the present invention.

The system 100 also includes a controller 140 adapted for, among other things, receiving and processing data related to the pre-operatively acquired image volume, the pre-operatively measured location of each fiducial marker and the intra-operatively monitored location of the distal end portion of the surgical instrument so as to guide the surgical instrument 120 along a predetermined path to open an access to the cochlea of the patient. The controller 140 is programmed to perform the steps of identifying a centroid of each fiducial marker in the pre-operatively acquired image volume, registering the identified centroid of each fiducial marker in the pre-operatively acquired image volume to the pre-operatively measured location of the corresponding fiducial marker in the anatomic space so as to determine a registration transformation, and mapping the intra-operatively monitored location of the distal end portion of the surgical instrument in the anatomic space onto a corresponding location in the pre-operatively acquired image volume by an inverse of the registration transformation, thereby intra-operatively displaying the location of the distal end portion of the surgical instrument. Furthermore, the controller 150 can be programmed to perform the step of disabling the surgical instrument when the surgical instrument departs from the predetermined path through a disabling device (not shown) associated with the surgical instrument.

As shown in FIG. 2A, the system 100 has an image displaying device 150, such as a monitor, in communication with the controller 140 for intra-operatively displaying the location of the distal end portion of the surgical instrument in the pre-operatively acquired image volume.

Figure 7:
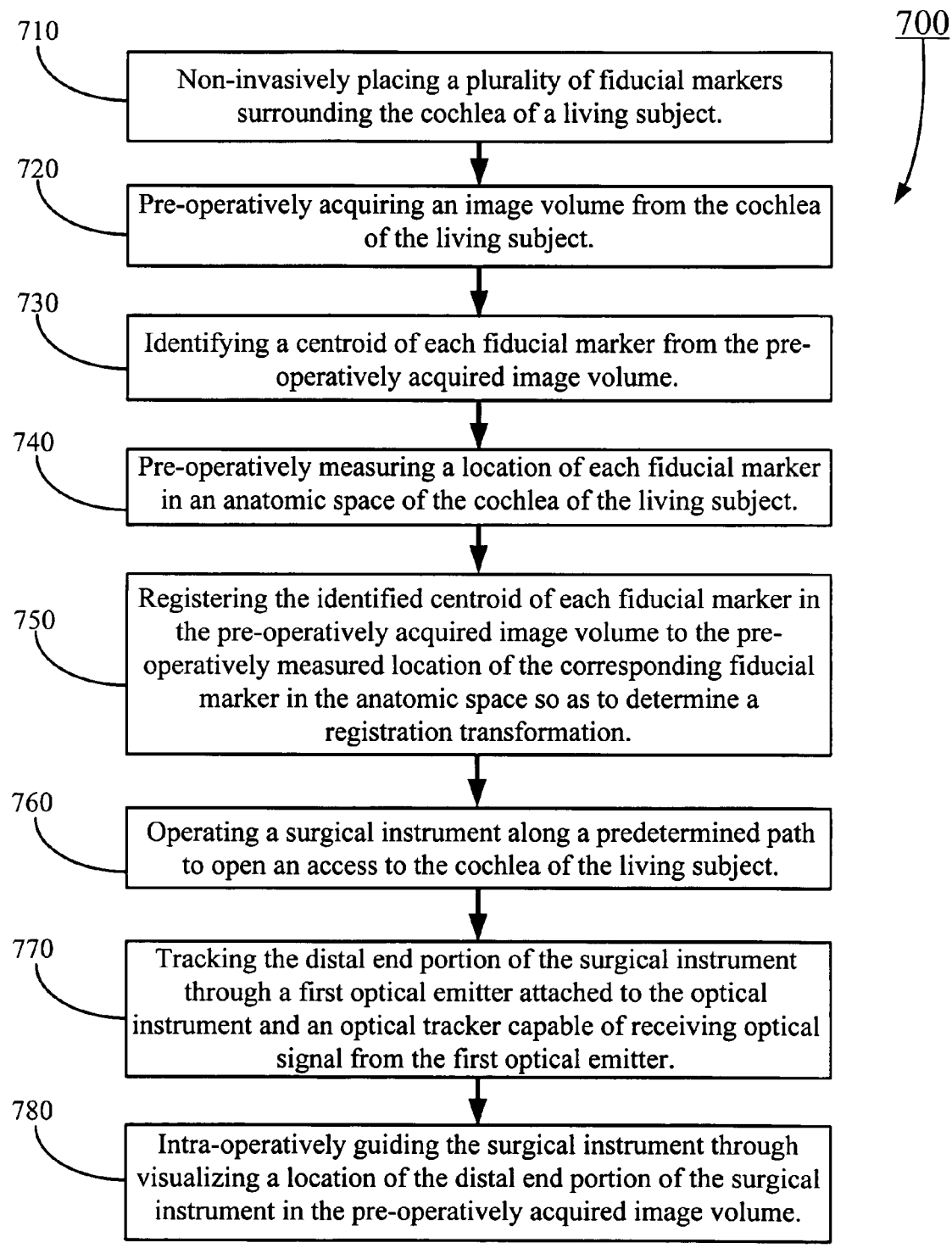
FIG. 7 shows a flowchart for providing an access to the cochlea of a living subject for performing a medical procedure according to one embodiment of the present invention.

Referring now to FIG. 7, a method for providing an access to the cochlea of a living subject for performing a medical procedure is shown according to one embodiment of the present invention. The method includes the following steps: at step 710, a plurality of fiducial markers are non-invasively placed around the ear portion of the patient. In one embodiment, it is implemented by mounting an LADS with an attached fiducial frame onto a maxilla of the patient, where the fiducial frame contains the plurality of fiducial markers, as discussed above, an EarMark™ system can be employed for non-invasively placing the fiducial markers around the ear portion of the patient. At step 720, one or more image volumes are acquired pre-operatively from the ear portion of the living subject wearing the LADS and fiducial frame, where the pre-operatively acquired image volumes contain the image of the fiducial markers. The fiducial frame is removed from and reattached to the LADS between two CT imaging scans. Multiple CT imaging scans are necessary in determining fiducial registration error (hereinafter "FRE") of the image space, which is employed to determine TRE. These FREs are averaged using sum of squares to determine an average FRE. At step 730, a centroid of each fiducial marker is identified from the pre-operatively acquired image volumes. In one embodiment, the image volumes (3D CT images) are reconstructed from the CT imaging scans by utilizing a high-performance computer. On these reconstructed image volumes, voxels (i.e., a surgical site) that lie within the ear portion of the living subject are selected by the surgeon. In other words, a surgical excavation, i.e., a mastoidectomy, is pre-operatively planned based on the radiographic images.

After pre-operatively acquiring image volumes of the patient, the LADS and the fiducial frame are removed and saved for the patient. In the OR, after performing a general anesthesia, the living subject is re-fitted with his/her customized LADS and the fiducial frame. A location of each fiducial marker in an anatomic space of the ear portion of the living subject is measured using an infrared optical tracking system, such as Polaris®, at step 740. The identified centroid of each fiducial marker in the pre-operatively acquired image volume is registered to the pre-operatively measured location of the corresponding fiducial marker in the anatomic space at step 750. The image registration determines a registration transformation and is performed by a computer/controller in conjunction with the infrared optical tracking system and customized software such as Voyger®(Z-Kat Inc., Hollywood, Fla.). The registration transformation, in one embodiment, includes a rigid-body transformation.

At step 760, a surgical instrument such as a surgical drill or surgical scalpel is operated along a predetermined path to open an access to the cochlea of the patient. The surgical instrument has a distal end portion. The distal end portion of the surgical instrument is intra-operatively tracked/monitored in the anatomic space of the ear portion of the living subject at step 770. The anatomic space of the ear portion of the living subject is corresponding to the OR. The intra-operatively monitored location of the distal end portion of the surgical instrument in the anatomic space is mapped onto a corresponding location in the pre-operatively acquired image volume by an inverse of the registration transformation. The monitoring of the location of the distal end portion of the surgical instrument is performed by the infrared optical tracking system. The infrared optical tracking system has a first infrared emitter attachable to the surgical instrument, a second infrared emitter attachable to the LADS mounted to the skull of the living subject, and an optical tracker adapted for receiving optical signals from the first optical emitter and the second optical emitter. The mapping step in one embodiment is performed with the computer. At step 780, the surgical instrument is intra-operatively guided through visualizing the location of the distal end portion of the surgical instrument in the pre-operatively acquired image volume. Furthermore, the skull of the living subject, or at least a portion of it, is intra-operatively tracked through the infrared optical tracking system by the second infrared emitter attached to the LADS that is mounted to the skull. Additionally, when the surgical instrument departs from the predetermined path, a controller, such as a computer coupled with the surgical instrument, generates a signal to disable the surgical instrument. Software codes and electric circuits for controlling the surgical instrument in the present invention are custom-designed.

According to the present invention, an accurate access to the middle ear via the facial recess without violating the canal of the facial nerve, the horizontal semicircular canal, or the external auditory canal is achieved by utilizing a non-invasively fiducial system in conjunction with a tracked otologic drill, thereby making percutaneous cochlear implantation technically feasible and doable. Because of the minimally invasive nature of the procedure, the surgery time is reduced dramatically, and the patient may not suffer from post-operative swelling. Furthermore, at time of surgery, a cochlear implant device can be activated and the patient may be asked if the device sounds better in the position, or after advancing it in a little further, or in a different position.

Without intent to limit the scope of the invention, further exemplary methods and their related results according to the embodiments of the present invention are given below.

Examples of the Invention

In the exemplary experiment provided herein it was proved that, given the systems accuracy, the middle ear may be safely accessed via the facial recess using a single drill hole from the lateral aspect of the mastoid cortex. The clinical correlation of this may be a percutaneous cochlear implant or other medical devices.

To facilitate an image-guided otologic surgery according to the present invention, a fiducial frame, an EarMark™ system developed by the inventors [9-11], is adapted for placing a plurality of fiducial markers in close proximity to the temporal bone of a patient in a non-invasive fashion, as shown in FIG. 1A. The EarMark™ system 114 is secured to a skull 119 of the patient by mounting the LADS 112 onto the maxilla of the patient. The use of the EarMark™ system in conjunction with a commercially-available IGS system enables submillimetric accuracy within the temporal bone to be achieved. For example, with this system, for over 234 target registrations, TRE was 0.76 mm with a standard deviation of 0.23 mm. Additionally, two human skulls: Skull No. 1 and Skull No. 2, were employed to practice the present invention. Other fiducial frames can also be used to practice the invention.

As shown in FIGS. 1 and 2, a human skull 119 (Skull No. 1 or Skull No. 2) was fitted with a dental bite block—the LADS 112 [12, 13] and placed on a surgical platform 190 in an operation room (OR) that is corresponding to the anatomic space of the patient. Affixed to the LADS 112 was the EarMark™ fiducial system 114 with fiducial markers 115 placed around the temporal bone as shown in FIG. 1A. This unit that includes the skull 119, LADS 112 and EarMark™ 114 was then scanned by a CT imaging scanner using clinically-applicable, temporal bone algorithms with a slice thickness=0.5 mm. The CT scanned data as well as the skull 119 were transported to a laboratory, where the CT scanned data was loaded onto commercially available software, such as Voyager®, for accurate identification of the centroids of the fiducial markers [14].

As shown in FIG. 2, the image-guided otologic surgery setup 100 has an infrared tracking system 130 with optical triangulation, such as a commercially-available Polaris® infrared tracking system, which communicates with image analysis and visualization software, for example, Voyagers®, running on a personal computer 140. To allow navigation during the operative intervention, the operative or surgical instrument, an otologic drill 120, was fitted with an infrared emitter 132. This drill 120 was registered to the system 100 so that the tip 122 of the drill 120 was tracked in real time on a video monitor 150. The skull 119 was also fitted with an infrared emitter 134.

Using the drill 120 as a localizing probe, the positions of the fiducial markers 115 on the EarMark™ system 114 were determined. Rigid registration between physical space (the OR) and radiographic space (the CT scanned image) was performed using the fiducial markers 115 on the EarMark™ system 114. Using the algorithm described [13], a rigid tranformation was calculated by minimizing the differences in position of the fiducial markers as identified on the CT scanned image with those identified in the OR. This transformation was then applied to all data points in the CT scanned image in mapping the CT scanned image to the physical space that the skull 119 was occupied in the OR. The IGS navigation was thus enabled with the drill 120 serving as a localizer and the video monitor 150 showing the corresponding position in the pre-operative CT scanned image which was actively updated in axial, coronal, and saggital views.

After registration was complete, the EarMark™ system 114 was removed from the LADS 112, and the infrared emitter 134 was then attached to the LADS 112, which allowed unimpeded surgical access to the temporal bone, as shown in FIG. 2B. As both the drill 120 and skull 119 were being actively tracked, each could be moved independently of the other while continuously tracking, as shown in FIG. 2B.

Using this IGS system and tracked otologic drill fitted with a 2 mm cutting bit, a percutaneous approach to the middle ear via the facial recess was undertaken. The drill was advanced by watching the video monitors which actively updated its position in the CT scanned image. Care was taken to avoid vital structures—the canal of the facial nerve, the horizontal semicircular canal, and the external auditory canal. With entry into the middle ear the drill bit could be seen via the external auditory canal. Next, the mastoid was drilled in a conventional fashion preserving the tunnel through which the percutaneous drill pass had been made. Photo documentation was performed to confirm that the track of the drill was corresponding to that shown in the CT scanned image.

Figure 3:
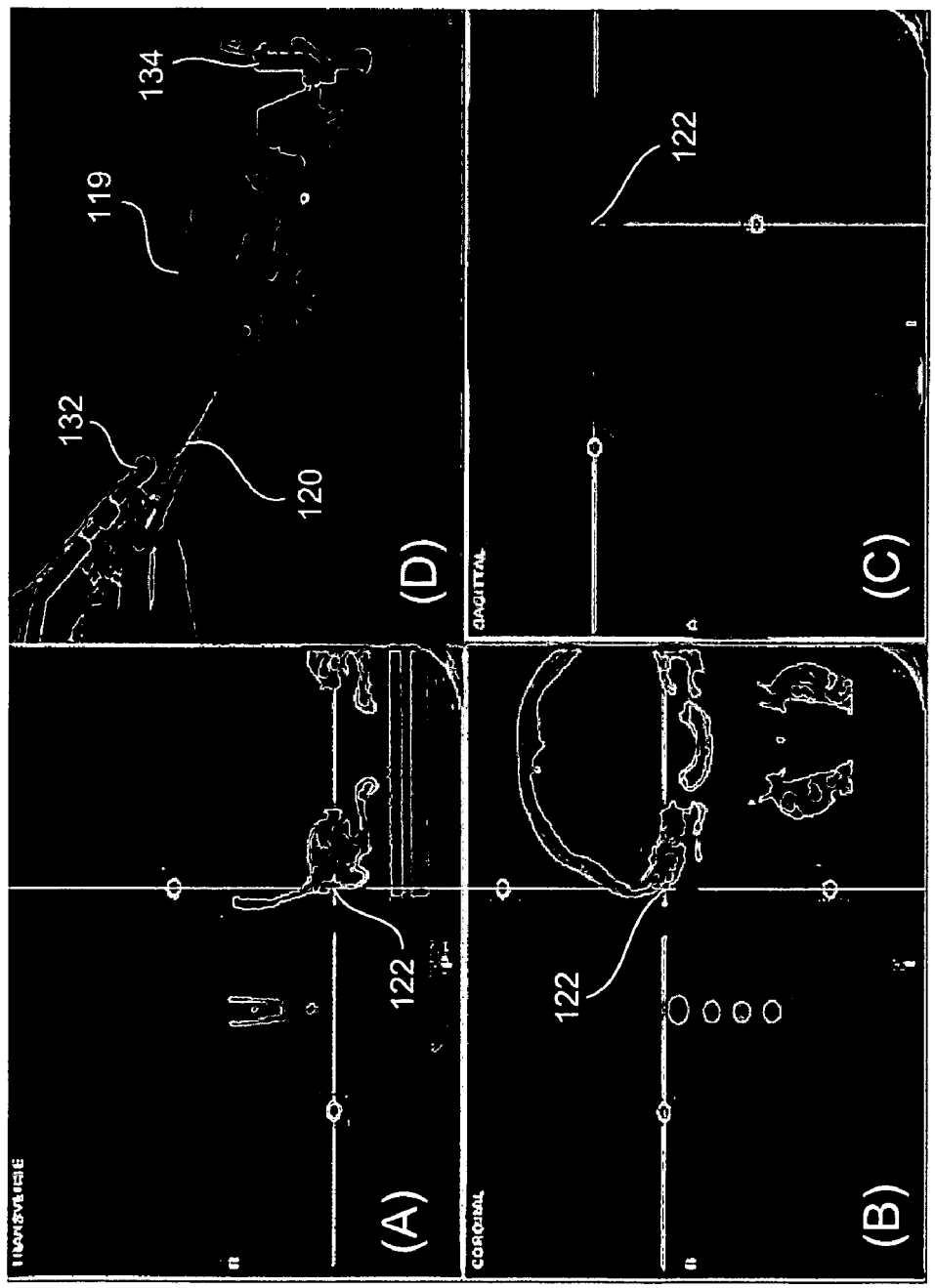
FIG. 3 shows a surgical navigation with IGS according to one embodiment of the present invention: (A) a transverse, (B) a coronal and (C) a sagittal view of the surgical field of interest visualized in the monitor, where the distal end portion of the surgical tool is localized on the pre-operatively obtained CT scanned image, and (D) a photograph of the skull with the surgical tool coupled with an infrared emitter.
Figure 4:
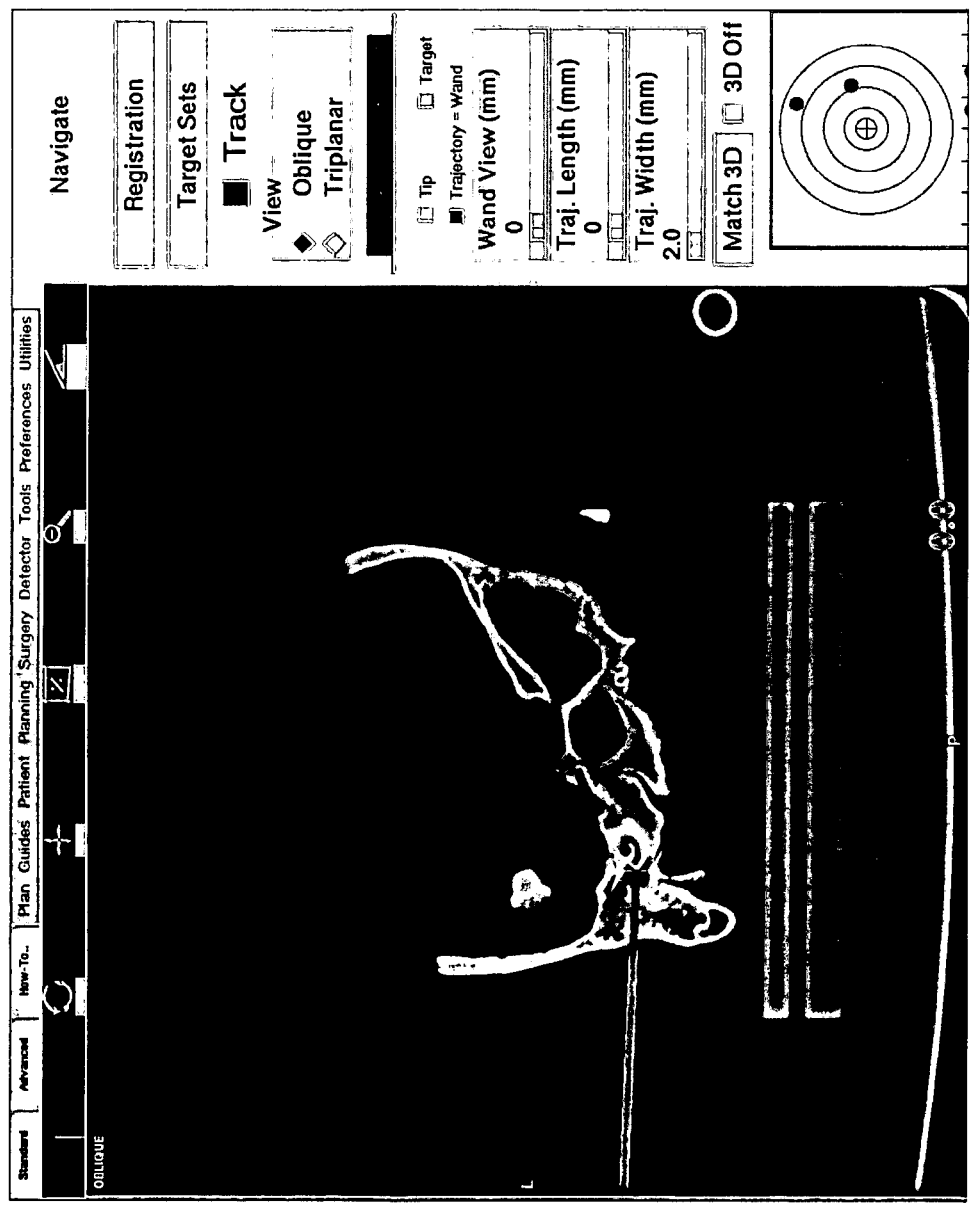
FIG. 4 shows a magnified oblique image with the drill path shown as a wide line. This path can be seen approaching the basal turn of the cochlea. The stylomastoid foramen can be seen inferior to this.

FIG. 3 demonstrated a composite of the experimental procedure. Panel (D) showed the skull 119 affixed with the infrared emitter 134 having the minimally-invasive, image-guided surgical procedure being performed. The drill 120 was tracked by the infrared emitter 132 while the skull 119 was tracked by the infrared emitter 134 during operation. This configuration allowed movement of either the skull 119 and/or the drill 120 independent of each other. Panels (A)-(C) showed respectively a transverse, coronal and sagittal view of the surgical site visualized in the video monitor, monitoring the current position 122 of the tip end of the drill 120 that was registered to the CT scanned image. The position 122 of the tip end of the drill 120 was identified by the crosshairs in these panels (A)-(C). For each set-up, fiducial registration error was calculated to be less than 0.8 mm and TRE was calculated to be less than 0.7 mm. FIG. 4 showed an additional, optional view—an oblique magnified view with tracking of the drill. A wide line showed the path of the drill as it approached the basal turn of the cochlea. The stylomastoid foramen was visible just below the path showing the distal, anterior-inferior course of the facial nerve.

Figure 5:
FIG. 5 shows photographs of surgical dissection of Skull No. 1 according to one embodiment of the present invention: (A) and (B) showing the path of the image-guided drill as it enters the middle ear via the facial recess, and (C) and (D) showing the same skull after traditional masotidecotmy preserving the path of the drill. In these panels, the vertical wire is located in the stylomastoid foramen and the horizontal wire passes through the drill path.

FIGS. 5A and 5B were photographic images of Skull No. 1 taken after minimally-invasive, image-guided, facial-recess approach to the middle ear according to the present invention. For the sake of illustration, a wire 510 extended down the drilled tunnel 520, as shown in FIG. 5A. A view down the drilled tunnel 520 into the middle ear was shown in FIG. 5B. FIGS. 5C and 5D were photographic images of Skull No. 1 taken after traditional mastoidectomy with preservation of the drill path. As illustrated in FIGS. 5C and 5D, the vertical wire 512 was placed in the stylomastoid foramen and the horizontal wire 514 was placed through the tunnel. When turned anteriorly, as shown in FIG. 5D, the tunnel was noted to cross anterior to the facial nerve within the confines of the facial recess.

Figure 6:
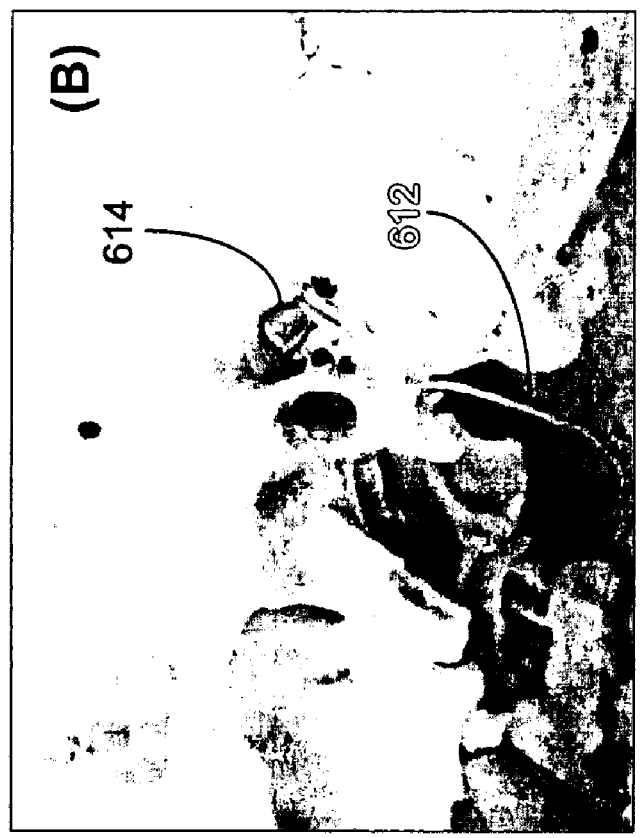
FIG. 6 shows photographs of surgical dissection of Skull No. 2 according to one embodiment of the present invention: (A) showing the path of the image-guided drill as it enters the middle ear via the facial recess. A wire has been feed through this tunnel, and (B) showing the post-mastoidectomy drilling with exposure of the semicircular canals (arched wire), sigmoid sinus, and facial canal (vertical wire). The drill path does not violate any of these structures.
Figure 6:
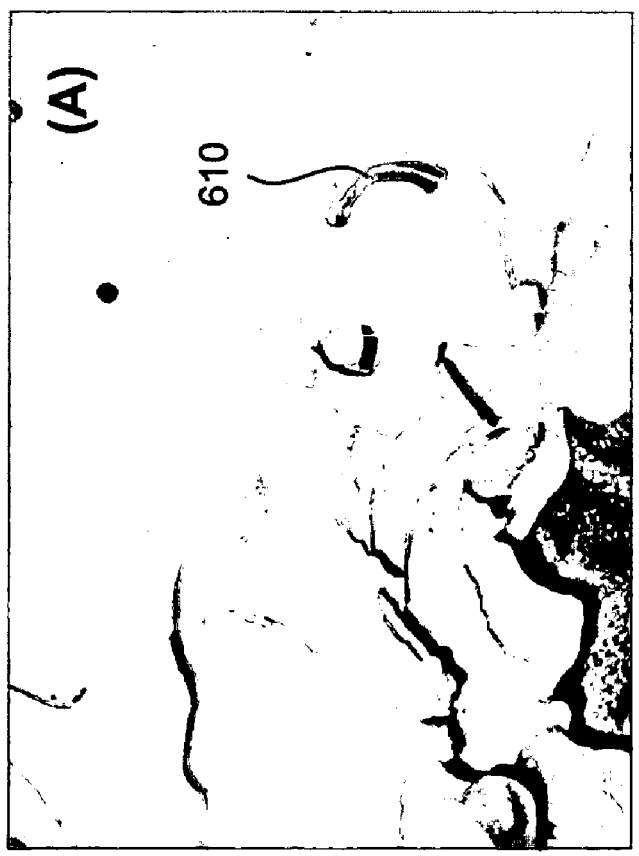

FIG. 6 showed photographic images of Skull No. 2, where the image after the minimally-invasive, image-guided, facial-recess approach to the middle ear with a wire 610 passing through the drilled tunnel 620 was shown in FIG. 6A, while FIG. 6B showed the result after mastoidectomy with exposure of vital structures. The vertical wire 612 is located in the facial canal, the arched wires 614 are in the semicircular canals, and bone over the central portion of the sigmoid sinus has been removed. Same as Skull No. 1, no vital structures were mechanically damaged by the image-guided drilling according to the present invention.

In sum, the present invention, among other things, discloses a method and system that utilize the non-invasively fiducial system with IGS systems to achieve the submillimetric accuracy for image-guided otologic/neurotologic surgery. Using this system in conjunction with a tracked otologic drill, the middle ear was approached via the facial recess using a single drill hole from the lateral aspect of the mastoid cortex. The path of the drill was verified by subsequently performing a traditional temporal bone dissection preserving the tunnel of bone through which the drill pass had been made.

The present invention thus provides an accurate approach to the middle ear via the facial recess without violating the canal of the facial nerve, the horizontal semicircular canal, or the external auditory canal. The exemplary results suggest that medical procedures such as percutaneous cochlear implantation are technically feasible. Cochlear implantation via mastoidectomy with extended facial recess is associated with a low incidence of complications and a high incidence of success [16, 17]. Because of the minimally invasive nature of the procedure without post-operative swelling, the cochlear implant device could be activated at time of surgery and the patient could go home hearing shortly after the surgery, which is a dramatic difference from the convertional system where patients waits 2-3 weeks to be activated.

The present invention also provides an additional layer of safety for otologic/neurotologic procedures. The active tracking of an otologic drill allows triggering of alarms or other safety mechanisms should a surgical border be approached or a predetermined surgical path be departed. One of mechanisms according to the present invention is shutting off the surgical drill to prevent damage to collateral tissue [18]. Analogous to the facial nerve monitor, such safety systems may allow more aggressive dissections while minimizing damage to vital structures.

Additionally, image-guided otologic surgery according to the present invention may prompt reworking of the current paradigm of wide surgical exposure for otologic/neurotologic procedures. Approaches to the petrous apex may be accomplished under minimally-invasive conditions. Retrofacial approach to the sinus tympani may be feasible during routine chronic middle ear surgery. This new paradigm may also include integration of other exciting technologies such as robotic surgery in the form of robotic mastoidectomy.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCES

[1]. Roberts D W, Strohbehn J W, Hatch et al. A frameless sterotaxic integration of computerized tomographic graphic imaging and the operating microscope. J Neurosurg 1986; 65:45-49.

[2]. Weinberg J S, Lang F F, and Sawaya R. Surgical management of brain metastases. Curr Oncol Rep 2001, 3(6): 476-83.

[3]. Wisoff J H, Boyett J M, Berger M S, Brant C, LI H, Yates A J, McGuire-Cullern P, Turski P A, Sutton L N, Allen J C, Packer R J, and Finlay J L. Current neurosurgical management and the impact of the extent of resection in the treatment of malignant gliomas of childhood: a report of the Children's Cancer Group trial no. CCG-945. J of Neurosurgery 1998, 89(1):52-9.

[4]. Sargent E W and Bucholz R D. Middle cranial fossa surgery with image-guided instrumentation. Otolaryngol Head Neck Surg 1997; 117:131-4.

[5]. Raine C H, Strachan D, and Gopichandran T. How we do it: Using a surgical navigation system in the management of the ossified cochlea. Cochlear Implants International 2003; 4:96-101.

[6]. Caversaccio M, Romualdez J, Vaecgker R m et al. Valuable use of computer-aided surgery in congenital bony aural atresia. J Laryngol Otol 2003; 117:241-8.

[7]. Raabe A, Krishnan R, Wolff R, Hermann E, Zimmermann M, Seifert V. Laser surface scanning for patient registration in intracranial image-guided surgery. Nuerosurgery 2002; 50:797-803.

[8]. Schlaier J, Warnat J, Brawanski A. Registration accuracy and practicability of laser-directed surface matching. Comput Aided Surg 2002; 7:284-290.

[9]. Labadie R F, Shah R J, Harris S S, Cetinkaya E, Haynes D S, Fenlon M, Juscyzk S, Galloway R L, Fitzpatrick J M. Image—Guided Otologic Surgery: Submillimeter Accuracy within the Temporal Bone. Otolaryngology-Head and Neck Surgery (in submission). Presented at the 2003 Annual Meeting of the American Academy of Otolaryngology Head and Neck Surgery, Orlando, Fla., September 21-24.

[10]. Labadie R F, Fenlon M, Devikalp H, et al. Image-guided otologic surgery. Computer Assisted Radiology and Congress and Exhibition (eds: Lemke H U, Vannier M W, Inamura K, Farman A G, Doi K, Reiber J H C) pp. 627-32. Elsevier Science, Amsterdam, The Netherlands, 2003.

[11]. Labadie R F, Shah R J, Harris S S, Cetinkaya E, Haynes D S, Fenlon M, Juscyzk S, Galloway R L, Fitzpatrick J M. Submillimetric Target-Registration Error using a Novel, Non-Invasive Fiducial System (the EarMark™) for Image Guided Otologic Surgery. Comp Aided Surg (in submission). Presented at the 17th International Congress and Exhibition of Computer Assisted Radiology and Surgery, London, England, June 25-28.

[12]. Fenlon M R, Jusczyzck A S, Edwards P J, and King A P. Locking acrylic resin dental stent for image guided surgery. J of Prosthet Dent 2000; 83:482-5.

[13]. Edwards P J, King A P, Maurer C R, et al. Design and evaluation of a system for microscope-assisted guided interventions (MAGI). IEEE Trans Med Imag 2000; 19:1082-1093.

[14]. ang M Y, Maurer Jr. C R, Fitzpatrick J M, and Maciunas R J. An automatic technique for finding and localizing externally attached markers in CT and MR volume images of the head. IEEE Trans Biomed Eng 1996; 43:627-37.

[15]. Fitzpatrick J M, West J M, Maurer Jr. C R. Predicting error in rigid-body, point-based registration. IEEE Trans Med Imaging 17, 694-702, 1998.

[16]. Cohen N L, Hoffman R A, Stroschein M. Medical or surgical complication related to the nucleus multichannel cochlear implant. Ann Itol Rhinol Laryngol 1988; 97:8-13.

[17]. Kronenberg J, Baumgartner W, Migirov L, et al. The suprameatal approach: an alternative surgical approach to cochlear implantation. Otol Neurotol 2004; 25:41-45.

[18]. Labadie R F and Fitzpatrick J M, Surgical Instrument Disablement Via Image-Guided Position Feedback, Patent Pending (filed 3-22-04).

What is claimed is:

1. A method for providing an access to a cochlea of a living subject, comprising the steps of:

(a) non-invasively placing a plurality of fiducial markers surrounding the cochlea of the living subject through mounting a locking dental acrylic resin splint (LADS) with an attached fiducial frame onto a maxilla of the living subject, wherein the fiducial frame is adapted for receiving the plurality of fiducial markers;

(b) pre-operatively acquiring an image volume of the cochlea of the living subject, the pre-operatively acquired image volume containing the image of the plurality of fiducial markers;

(c) identifying a centroid of each fiducial marker from the pre-operatively acquired image volume;

(d) pre-operatively measuring a location of each fiducial marker in an anatomic space of the cochlea of the living subject;

(e) registering the identified centroid of each fiducial marker in the pre-operatively acquired image volume to the pre-operatively measured location of the corresponding fiducial marker in the anatomic space so as to determine a registration transformation;

f) determining the location of anatomical structures of the living subject from the image volume, wherein the anatomical structures include the canal of the facial nerve, the horizontal semicircular canal, and the external auditory canal;

(g) determining a single linear path from the lateral edge of the skull to the cochlea of the living subject which avoids the anatomical structures;

(h) operating a surgical instrument along the linear path to open an access to the cochlea of the living subject, the surgical instrument having a distal end portion;

(i) tracking the distal end portion of the surgical instrument through a first optical emitter attached to the optical instrument and an optical tracker adapted for receiving optical signal from the first optical emitter;

(j) intra-operatively guiding the surgical instrument through visualizing a location of the distal end portion of the surgical instrument in the pre-operatively acquired image volume; and (k) intra-operatively tracking at least a portion of the skull of the living subject through a second optical emitter attached to the LADS and the optical tracker adapted for receiving optical signal from the second optical emitter.

2. The method of claim 1, wherein the pre-operatively acquiring step is performed with an imaging acquisition device.

3. The method of claim 1, wherein the pre-operatively measuring step is performed with a localizing probe.

4. The method of claim 3, wherein the localizing probe is coupled with the first optical emitter.

5. The method of claim 1, wherein the operating step is performed by a human being.

6. The method of claim 1, wherein the operating step is performed at least in part by a man-made device.

7. The method of claim 1, wherein the intra-operatively guiding step comprises the steps of:

(a) intra-operatively monitoring the location of the distal end portion of the surgical instrument in the anatomic space of the cochlea of the living subject; and (b) mapping the intra-operatively monitored location of the distal end portion of the surgical instrument in the anatomic space onto a corresponding location in the pre-operatively acquired image volume by an inverse of the registration transformation.

8. The method of claim 7, wherein the intra-operatively monitoring step is performed with the first optical emitter and the optical tracker.

9. The method of claim 1, further comprising the step of disabling the surgical instrument when the surgical instrument departs from the predetermined path.

10. The method of claim 1, further comprising the step of performing a therapeutic medical procedure or a diagnosis medical procedure through the access to the cochlea of the living subject.

11. The method of claim 10, wherein the therapeutic medical procedure comprises a medical procedure for placement of one of a cochlear implant, a drug delivery system, a carrier device, a medical detecting system, a medical treatment system, and any combination of them.

12. The method of claim 10, wherein the diagnosis medical procedure comprises a medical procedure for using a medical device to detect and collect information related to the living subject.

13. A method for providing an access to a cochlea of a living subject, comprising the steps of:
  (a) non-invasively placing a plurality of fiducial markers surrounding the cochlea of the living subject;
  (b) pre-operatively acquiring an image volume of the cochlea of the living subject, the pre-operatively acquired image volume containing the image of the plurality of fiducial markers;
  (c) identifying a centroid of each fiducial marker from the pre-operatively acquired image volume;
  (d) pre-operatively measuring a location of each fiducial marker in an anatomic space of the cochlea of the living subject;
  (e) registering the identified centroid of each fiducial marker in the pre-operatively acquired image volume to the pre-operatively measured location of the corresponding fiducial marker in the anatomic space so as to determine a registration transformation;
  (f) determining the location of anatomical structures of the living subject from the image volume, wherein the anatomical structures include the canal of the facial nerve, the horizontal semicircular canal, and the external auditory canal;
  (g) determining a single linear path from the lateral edge of the skull to the cochlea of the living subject which avoids the anatomical structures;
  (h) operating a surgical instrument along the linear path to open an access to the cochlea of the living subject, the surgical instrument having a distal end portion;
  (i) tracking the distal end portion of the surgical instrument through a first optical emitter attached to the optical instrument and an optical tracker adapted for receiving optical signal from the first optical emitter; and
  (j) intra-operatively identifying a real-time position of the distal end portion of the surgical instrument by crosshairs in panels showing respectively a transverse, coronal and sagittal view of the surgical site visualized in an image displaying device.

14. A method for providing an access to a cochlea of a living subject, comprising the steps of:
  (a) non-invasively placing a plurality of fiducial markers surrounding the cochlea of the living subject;
  (b) pre-operatively acquiring an image volume of the cochlea of the living subject, the pre-operatively acquired image volume containing the image of the plurality of fiducial markers;
  (c) identifying a centroid of each fiducial marker from the pre-operatively acquired image volume;
  (d) pre-operatively measuring a location of each fiducial marker in an anatomic space of the cochlea of the living subject;
  (e) registering the identified centroid of each fiducial marker in the pre-operatively acquired image volume to the pre-operatively measured location of the corresponding fiducial marker in the anatomic space so as to determine a registration transformation;
  (f) determining the location of anatomical structures of the living subject from the image volume, wherein the anatomical structures include the canal of the facial nerve, the horizontal semicircular canal, and the external auditory canal;
  (g) determining a single linear path from the lateral edge of the skull to the cochlea of the living subject which avoids the anatomical structures;
  (f) operating a surgical instrument along the linear path to open an access to the cochlea of the living subject, the surgical instrument having a distal end portion;
  (i) tracking the distal end portion of the surgical instrument through a first optical emitter attached to the optical instrument and an optical tracker adapted for receiving optical signal from the first optical emitter;
  (j) intra-operatively guiding the surgical instrument in real time through visualizing a location of the distal end portion of the surgical instrument in the pre-operatively acquired image volume as displayed on an image displaying device; and
  (k) intra-operatively identifying a real-time position of the distal end portion of the surgical instrument by crosshairs in panels showing respectively a transverse, coronal and sagittal view of the surgical site visualized in the image displaying device.

* * * * *

UNITED STATES PATENT AND TRADEMARK OFFICE
CERTIFICATE OF CORRECTION

PATENT NO. : 8,380,288 B2
APPLICATION NO. : 11/413254
DATED : February 19, 2013
INVENTOR(S) : Robert F. Labadie et al.

Page 1 of 1

It is certified that error appears in the above-identified patent and that said Letters Patent is hereby corrected as shown below:

On the Title Page, Item (54) and in the Specification, Column 1, Title:
"SYSTEM AND METHODS OF USING IMAGE-GUIDANCE FOR PROVIDING AN ACCESS TO A COCHLEAR OF A LIVING SUBJECT",
should read --SYSTEM AND METHODS OF USING IMAGE-GUIDANCE FOR PROVIDING AN ACCESS TO A COCHLEA OF A LIVING SUBJECT--

Signed and Sealed this
Thirteenth Day of August, 2013

Teresa Stanek Rea
*Acting Director of the United States Patent and Trademark Office*